(12) United States Patent
Roell et al.

(10) Patent No.: US 12,357,511 B2
(45) Date of Patent: Jul. 15, 2025

(54) DISPOSABLE ABSORBENT ARTICLE (71) Applicant: The Procter & Gamble Company, Cincinnati, OH (US)

(72) Inventors: Stefan Roell, Bensheim (DE); Thomas Jan Bruehl, Frankfurt am Main (DE); Clint Adam Morrow, Union, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 18/321,812

(22) Filed: May 23, 2023

(65) Prior Publication Data

US 2023/0293359 A1 Sep. 21, 2023

Related U.S. Application Data

(63) Continuation of application No. 15/931,932, filed on May 14, 2020, now Pat. No. 11,696,858.
(Continued)

(51) Int. Cl.
*A61F 13/475* (2006.01)
*A61F 13/53* (2006.01)
(Continued)

(52) U.S. Cl.
CPC .......... *A61F 13/4756* (2013.01); *A61F 13/53* (2013.01); *A61F 13/84* (2013.01);
(Continued)

(58) Field of Classification Search
CPC ...... A61F 13/4756; A61F 13/53; A61F 13/84; A61F 2013/530007; A61F 2013/5312;
(Continued)

(56) References Cited

U.S. PATENT DOCUMENTS 4,773,905 A 9/1988 Molee et al.
5,807,365 A 9/1998 Luceri
(Continued)

FOREIGN PATENT DOCUMENTS

CN 1259335 A 7/2000
CN 1857187 A 11/2006
(Continued)

OTHER PUBLICATIONS

PCT Search Report and Written Opinion for PCT/US2020/070049 dated Jul. 30, 2020, 13 pages.
(Continued)

*Primary Examiner* — Susan S Su
*Assistant Examiner* — Ted Yang
(74) *Attorney, Agent, or Firm* — Anna E. Haller; Angela K. Haughey; Amanda Marie Herman Berghauer (57) ABSTRACT

A disposable absorbent article. The disposable absorbent article has a topsheet; a backsheet; and an absorbent core disposed between the topsheet and the backsheet. The disposable absorbent article may include embossed central channels, a perimeter channel, and a pair of rear channels disposed on opposite sides of a longitudinal axis transversely inboard of the perimeter channel and longitudinally outboard of the outwardly convex longitudinal channels. The pair of rear channels may be generally candy cane-shaped.

14 Claims, 9 Drawing Sheets

Related U.S. Application Data (60) Provisional application No. 62/848,086, filed on May 15, 2019.

(51) Int. Cl.
*A61F 13/531* (2006.01)
*A61F 13/84* (2006.01)

(52) U.S. Cl.
CPC .............. *A61F 2013/530007* (2013.01); *A61F 2013/5312* (2013.01); *A61F 2013/8402* (2013.01)

(58) Field of Classification Search
CPC . A61F 2013/8402; A61F 13/475; A61F 13/47
See application file for complete search history.

(56) References Cited

U.S. PATENT DOCUMENTS

| | | | |
|---|---|---|---|
| 6,563,013 B1* | 5/2003 | Murota | A61F 13/533 604/385.01 |
| 7,122,713 B2* | 10/2006 | Komatsu | A61F 13/4704 604/385.01 |
| 7,696,402 B2* | 4/2010 | Nishikawa | A61F 13/4758 604/385.101 |
| 9,655,788 B2 | 5/2017 | Ueminami et al. | |
| 10,512,566 B2 | 12/2019 | Park | |
| 10,779,998 B2 | 9/2020 | Miao et al. | |
| 11,364,158 B2 | 6/2022 | Lee | |
| 11,602,464 B2 | 3/2023 | Park | |
| 11,696,858 B2 | 7/2023 | Roell et al. | |
| 2003/0078553 A1 | 4/2003 | Wada | |
| 2003/0114807 A1 | 6/2003 | Underhill et al. | |
| 2004/0127875 A1 | 7/2004 | Hammons et al. | |
| 2004/0176734 A1 | 9/2004 | Rasmussen et al. | |
| 2004/0243082 A1* | 12/2004 | Kinoshita | A61F 13/47245 604/385.04 |
| 2005/0124951 A1 | 6/2005 | Kudo et al. | |
| 2005/0148970 A1 | 7/2005 | Kudo | |
| 2005/0148972 A1 | 7/2005 | Miyama et al. | |
| 2005/0148973 A1 | 7/2005 | Tamura et al. | |
| 2006/0100598 A1 | 5/2006 | Tamura et al. | |
| 2006/0116652 A1* | 6/2006 | Miura | A61F 13/47 604/385.101 |
| 2006/0116653 A1* | 6/2006 | Munakata | A61F 13/4702 604/385.101 |
| 2006/0276767 A1* | 12/2006 | Ueminami | A61F 13/533 604/385.101 |
| 2007/0073253 A1 | 3/2007 | Miyama et al. | |
| 2007/0191798 A1 | 8/2007 | Glaug et al. | |
| 2008/0065037 A1 | 3/2008 | Konawa | |
| 2008/0103467 A1 | 5/2008 | Wallstrom et al. | |
| 2008/0147024 A1 | 6/2008 | Potts et al. | |
| 2008/0281287 A1 | 11/2008 | Marcelo et al. | |
| 2009/0012489 A1* | 1/2009 | Francoeur | A61F 13/4756 604/385.01 |
| 2009/0099539 A1 | 4/2009 | Periman | |
| 2009/0292268 A1 | 11/2009 | Bagger-sjoebaeck et al. | |
| 2009/0312733 A1 | 12/2009 | Pellen | |
| 2009/0326502 A1 | 12/2009 | Konawa | |
| 2011/0092944 A1 | 4/2011 | Sagisaka et al. | |
| 2011/0130737 A1 | 6/2011 | Sagisaka et al. | |
| 2011/0251575 A1* | 10/2011 | Kuroda | A61F 13/4756 604/380 |
| 2011/0288514 A1 | 11/2011 | Kuroda et al. | |
| 2011/0319851 A1 | 12/2011 | Kudo et al. | |
| 2012/0035566 A1 | 2/2012 | Sagisaka et al. | |
| 2012/0109093 A1* | 5/2012 | Wilson | A61F 13/15756 604/385.05 |
| 2012/0220971 A1* | 8/2012 | Harada | A61F 13/4756 604/380 |
| 2012/0271268 A1 | 10/2012 | Suzuki et al. | |
| 2013/0060218 A1* | 3/2013 | Kudo | A61F 13/495 604/378 |
| 2013/0165885 A1* | 6/2013 | Kurihara | A61F 13/533 604/380 |
| 2013/0184665 A1 | 7/2013 | Kato et al. | |
| 2013/0226123 A1 | 8/2013 | Kudo et al. | |
| 2013/0267926 A1* | 10/2013 | Uematsu | A61F 13/4758 604/385.101 |
| 2013/0345656 A1 | 12/2013 | Kato et al. | |
| 2014/0358106 A1 | 12/2014 | Tan et al. | |
| 2015/0265474 A1 | 9/2015 | Munakata | |
| 2015/0335498 A1 | 11/2015 | Hubbard, Jr. et al. | |
| 2016/0089279 A1 | 3/2016 | Barbosa et al. | |
| 2016/0206482 A1 | 7/2016 | Nishikawa et al. | |
| 2016/0206483 A1 | 7/2016 | Nishikawa et al. | |
| 2016/0250084 A1* | 9/2016 | Umemoto | A61F 13/49001 604/380 |
| 2016/0317365 A1 | 11/2016 | Kurihara | |
| 2017/0119597 A1 | 5/2017 | Bewick-sonntag | |
| 2017/0246054 A1 | 8/2017 | Bishop et al. | |
| 2017/0333263 A1 | 11/2017 | Tashiro et al. | |
| 2017/0333265 A1 | 11/2017 | Hanao et al. | |
| 2018/0098895 A1* | 4/2018 | Hashino | A61F 13/5121 |
| 2019/0060141 A1 | 2/2019 | Di Berardino et al. | |
| 2019/0282414 A1* | 9/2019 | Kuramochi | A61F 13/47236 |
| 2021/0169707 A1* | 6/2021 | Suyama | A61F 13/4756 |

FOREIGN PATENT DOCUMENTS

| | | | |
|---|---|---|---|
| CN | 1929876 A | 3/2007 | |
| CN | 101951863 A | 1/2011 | |
| EP | 1330995 A2 | 7/2003 | |
| GB | 2256803 A | 12/1992 | |
| JP | 2002165837 A * | 6/2002 | ....... A61F 13/53427 |
| JP | 3781617 B2 * | 5/2006 | |
| JP | 2009207660 A | 9/2009 | |
| JP | 2010142460 A | 7/2010 | |
| JP | 2015104433 A | 6/2016 | |
| TW | 201302176 A * | 1/2013 | ....... A61F 13/15577 |
| TW | 201711653 A * | 4/2017 | ............ A61F 13/15 |
| WO | WO-2012090830 A1 * | 7/2012 | ....... A61F 13/15731 |
| WO | WO-2018235497 A1 * | 12/2018 | ............ A61F 13/47 |

OTHER PUBLICATIONS

All Office Actions; U.S. Appl. No. 15/931,932, filed May 14, 2020.

* cited by examiner

Figure 6A

DISPOSABLE ABSORBENT ARTICLE

CROSS REFERENCE TO RELATED APPLICATIONS

This application is a continuation of, and claims priority under 35 U.S.C. § 120 to, U.S. patent application Ser. No. 15/931,932, filed on May 14, 2020, which claims the benefit, under 35 USC § 119(e), of U.S. Provisional Patent Application Ser. No. 62/848,086, filed on May 15, 2019, the entire disclosures of which are fully incorporated by reference herein.

FIELD OF THE INVENTION

The present invention relates to absorbent articles such as sanitary napkins, pantiliners, and incontinence pads. More particularly, the present invention relates to absorbent articles having traverse reinforcing elements.

BACKGROUND OF THE INVENTION

Absorbent articles, such as sanitary napkins, pantiliners, and incontinence pads, are typically worn in the crotch region of an undergarment. These devices are designed to absorb and retain liquids and other discharges from the human body to prevent body and garment soiling. These types of absorbent articles are typically placed in a garment such as the wearer's panty and worn between the wearer's legs, adjacent to the genital (or fluids discharge source) area of the body.

Conventional relatively thick sanitary napkin products currently marketed provide some protection from soiling by utilizing a combination of increased product length and thickness (which may include a profiled or varied caliper). These products, however, are not believed to prevent leakage of body fluids perfectly in particular when the sanitary napkin is compressed by a strong compressive force which is sometimes applied by the body of the wearer when the absorbent article is worn. Thus, leakage is possible, particularly at the both sides of the central region, and sometimes at the front and/or rear regions of these products. This issue is seen not only in conventional relatively thick sanitary napkin products but also other conventional products such as relatively thinner and smaller sanitary napkins as well as other types of absorbent articles, e.g., pantiliners, diapers, and incontinence pads in the market.

Additionally, problems with these products can arise due to the stresses and strains imparted on the article particularly during movement of the wearer. e.g. walking. The stresses imparted onto these products can cause degradation of the absorbent core and/or separation of the constituent layer of the absorbent article. This, unfortunately, can increase the likelihood of leakage by the article.

Thus, there is a need for an absorbent article that provides improved integrity of the absorbent article.

SUMMARY OF THE INVENTION

A disposable absorbent article constructed in accordance with the present disclosure can provide a user with both comfort and conformity. Additionally, absorbent articles constructed in accordance with the present disclosure can increase the integrity of the article so that the stresses and strains caused by the movement of the wearer are better accommodated than that of conventional pads.

The disposable absorbent articles of the present disclosure comprise a topsheet; a backsheet; an absorbent core disposed between the topsheet and the backsheet. The disposable absorbent articles of the present disclosure can also exhibit a pad peel force of at least about 0.5 N, at least about 0.7 N, or at least about 1.0 N, when measured in accordance with the product integrity test.

DETAILED DESCRIPTION OF THE INVENTION

As used herein, "absorbent article" refers to articles which absorb and contain body exudates or discharges such as body fluids, and is intended to include sanitary napkins, pantiliners, diapers, and incontinence pads (and other articles worn in the crotch region of a garment) as well as diapers, training pants and pull-on diapers, briefs and the like.

Herein, "disposable article" refers to articles which are intended to be discarded after a single use, composted, or otherwise disposed of in an environmentally compatible manner. (That is, they are not intended to be laundered or otherwise restored or reused as an absorbent article.)

Herein, "sanitary napkin" refers to articles which are worn by females adjacent to the pudendal region which are intended to absorb and contain the various exudates which are discharged from the body (e.g., blood, menses, and urine). It should be understood, however, that the present invention is also applicable to other hygiene pads such as pantiliners, diapers, and incontinence pads worn in the crotch region of a garment.

Herein, "joined" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

Herein, "body surface" refers to surfaces of absorbent articles and/or their component members which face the body of the wearer, while "garment surface" refers to the opposite surfaces of the absorbent articles and/or their component members that face away from the wearer when the absorbent articles are worn. Absorbent articles and components thereof, including the topsheet, backsheet, absorbent core, and any individual layers of their components, have a body surface and a garment surface.

Herein, "fluids source area" refers to a part of specific area of the body surface of absorbent articles where the source of body fluids of the wearer is expected to come most closely when the absorbent article is worn.

Herein, "longitudinal" refers to a line, axis or direction in the plane of an absorbent article that is generally aligned with (e.g., approximately parallel to) a vertical plane which bisects a standing wearer into left and right body halves when the absorbent article is worn. Herein, "longitudinal axis" refers to a longitudinal axis that bisects the body surface of absorbent articles symmetrically along the line.

Herein, "transverse" or "lateral" refers to a line, axis or direction which lies within the plane of absorbent articles that is generally perpendicular to the longitudinal direction. Herein, "transverse axis" refers to a transverse axis that intersects the longitudinal axis at the center of the fluids source area.

Figure 1:
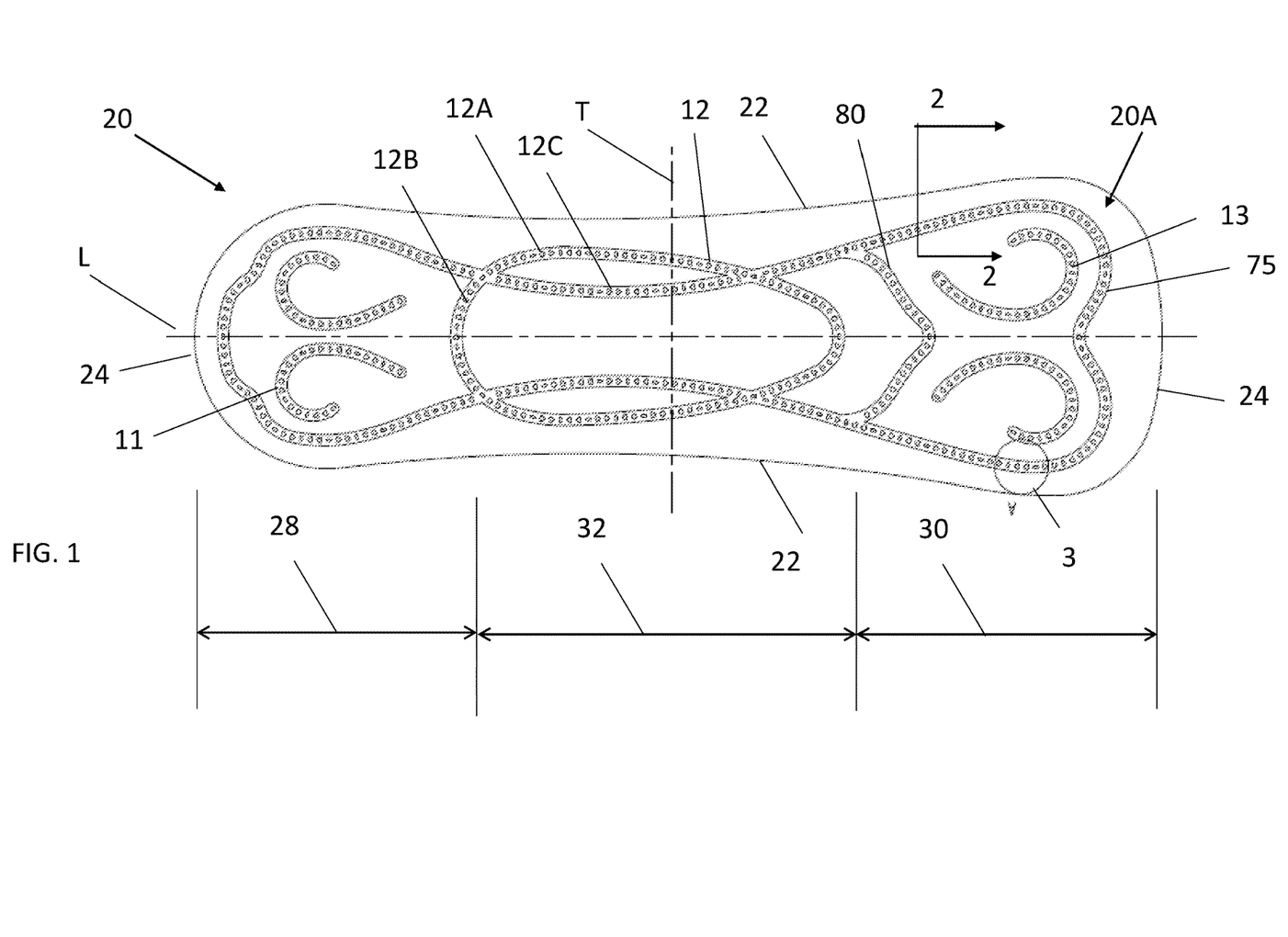
FIG. 1 is a schematic representation of an absorbent article constructed in accordance with the present disclosure shown in plan view.

FIG. 1 is a top plane view of an absorbent article of the present disclosure. A sanitary napkin 20 has two surfaces, a liquid pervious body surface (or body-contacting surface) 20A and a liquid impervious garment surface disposed opposite the liquid pervious body surface 20A. The body surface 20A is intended to be worn adjacent to the body of the wearer. The garment surface of the sanitary napkin 20 is on the opposite side and is intended to be placed adjacent to the wearer's undergarments when the sanitary napkin 20 is worn.

The sanitary napkin 20 has a longitudinal axis L and a transverse axis T. The sanitary napkin 20 has two spaced apart longitudinal edges 22 and two spaced apart transverse or end edges 24, which jointly form the periphery of the sanitary napkin 20. The sanitary napkin 20 also has two end regions, i.e., a front end region 28 and a rear end region 30. A central region 32 is disposed between the end regions 28 and 30. The sanitary napkin 20 may include a pair of central side flaps in the central region 32. Each flap can extend laterally outward from the longitudinal side edges 22 in the central region 32.

The front end region 28 is defined as the area that is placed to the front of the wearer's body when the sanitary napkin 20 is worn. The rear end region 30 is defined as the area that is placed to the rear of the wearer's body. The central region 32 is defined as the area that is generally located directly below the perineum of the wearer and includes the region of intended fluid entry of the sanitary napkin 20.

Specifically, the central region 32 ends at a longitudinal distance which is selected from a range of about 30 to about 105 mm, or from a range of about 50 to about 70 mm from the intersection of the longitudinal axis L and the transverse axis T of the sanitary napkin 20. As shown, the central region 32 ends at a longitudinal distance of about 58 mm from the intersection of the longitudinal axis L and the transverse axis T. In other words, each of the front and rear end regions 28 and 30 starts at that longitudinal distance from the intersection of the longitudinal axis and the transverse axis, respectively.

Figure 2:
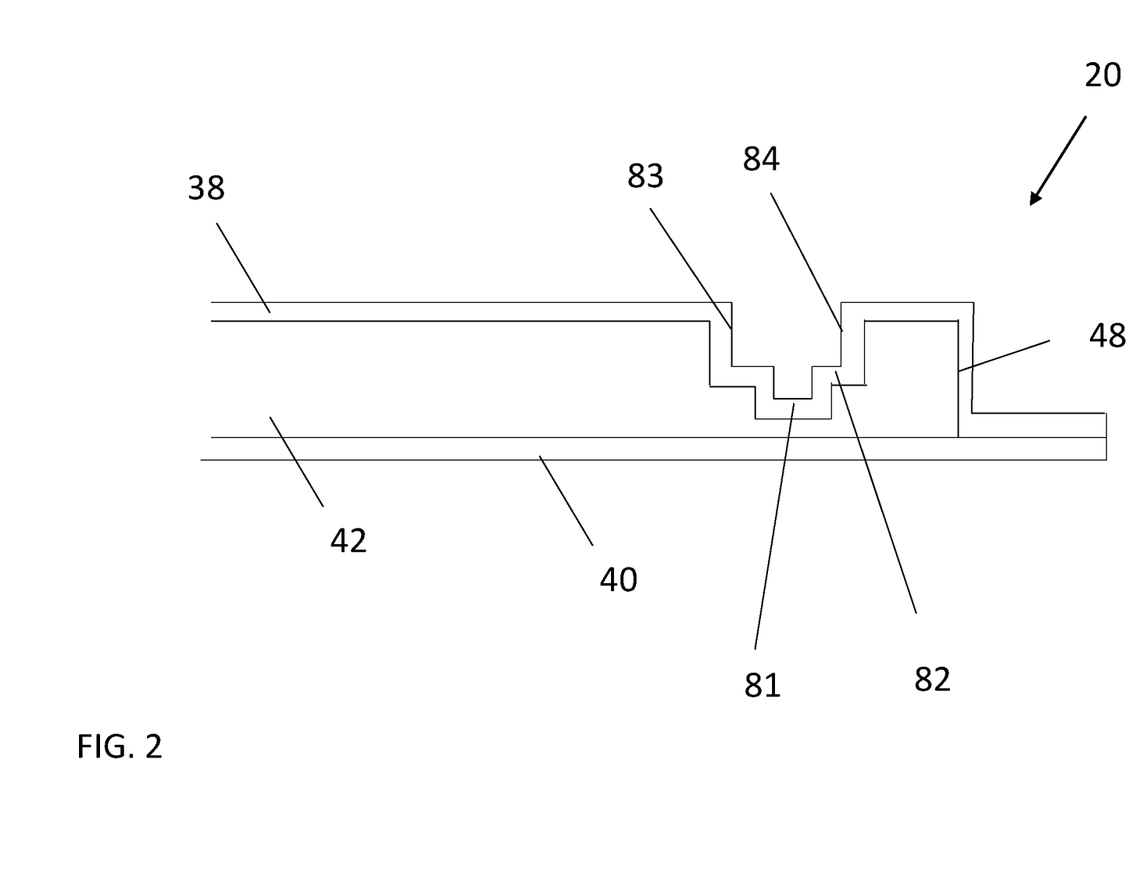
FIG. 2 is a schematic cross section of the absorbent article of FIG. 1 taken along line 2-2.

FIG. 2 is a cross-sectional view of the sanitary napkin 20 taken along the section line 2-2 in FIG. 1, which shows the individual components of the sanitary napkin 20 shown in FIG. 1. The sanitary napkin 20 shown in FIG. 2 generally comprises at least three primary components, i.e., a topsheet 38; a backsheet 40; an absorbent core 42 having longitudinal edges 48 disposed between the topsheet 38 and the backsheet 40. The topsheet 38, backsheet 40, and absorbent core 42 can comprise any types of materials known in the art as being suitable for such components.

Referring back to FIG. 1, the sanitary napkin 20 includes central channels 12 formed in the central region 32. Although, the central channel 12 can extend into the front end region 28 and/or the back end region 30 to some extent. The central channels 12 may include an oval channel which includes a pair of outwardly convex longitudinal channels 12A and a pair of outwardly convex transverse channels 12B. Herein, "outwardly convex" means a specified channel has a curved line shape (including a polygonal lines shape) which is outwardly extended when looking from the longitudinal or traverse axis L or T. The central channels 12 may also include, within the area surrounded by the oval channels, a pair of inwardly convex longitudinal channels 12C. Herein, "inwardly convex" means a specified channel has a curved line shape (including a polygonal lines shape) which is inwardly extended when looking from the longitudinal or traverse axis L or T. The design of the central channels 12 including the total number thereof, and the length and shape of each component channel can vary depending on the design of the sanitary napkin 20.

As shown, the central channels 12 may comprise continuous channels. For example, the longitudinal channels 12A and the transverse channels 12B may be connected to one another such that the central channel 12 is continuous. Alternatively, the longitudinal channels 12A and/or the transverse channels 12B may be discontinuous, e.g. discrete. And as shown, the convex longitudinal channels 12C may be part of a larger channel which extends into the front end region 28 and/or the back end region 30.

The oval channel 12 can take any oval like shapes which include, for example, an actual oval shape defined by mathematics and an eye shape (i.e., a shape formed by two are like lines), and the like. The longitudinal channels 12A can have a maximum length of between about 25 and about 205 mm, between about 60 and about 150 mm, or about 96 mm, specifically including all values within this range and any range created thereby. The transverse channels 12C can have a maximum length (in the transverse direction) between about 10 and about 75 mm, between about 35 and about 55 mm, or about 48 mm, specifically including all values within these ranges and any ranges created thereby.

The oval channel 12 is not always necessary but generally desired since it forms a generally closed area defined by the channel structure in the central region 32 that can contribute to retain body fluids absorbed by the absorbent core 42 within the area. Additionally, it is believed that the oval channel 12 also contributes to an increase in conformance of the sanitary pad 20. As the central region 32 is most closely associated with the area of the pad that is generally positioned between the legs of the wearer, this area of the pad should be provided with the ability to conform to the compressive forces that are applied by the thighs of the wearer.

Referring still to FIG. 1, the sanitary napkin 20 includes front channels 11 formed in the front end region 28, and rear channels 13 formed in the back end region 30. The front channels 11 include two concave candy-cane-shaped channels, while the rear channels 13 include two concave candy-cane-shaped channels. It is believed that the front channels 11 and the rear channels can help provide comfort and conformance to the sanitary napkin 20 in the front end region 28 and the back end region 30.

Additionally, the sanitary napkin 20 comprises a perimeter channel 75. The perimeter channel 75 as shown, can extend from the front end region 28, through the central region 32 and into the back end region 30. The front channels 11 may be enclosed by the perimeter channel 75 and the central channel 12. Or, the front channels 11 may be enclosed by the perimeter channel 75 and one of the transverse channels 12B which is disposed most proximal to the front end region 28. Similarly, the rear channels 13 can be enclosed by the perimeter channel 75 and one of the transverse channels that is most proximal to the back end region 30. As shown, the perimeter channel 75 can be the most outboard channel in the front end region 28 and the back end region 30.

The sanitary napkin 20 may further comprise a transverse reinforcement channel 80. As shown, the transverse reinforcement channel 80 may be disposed in the back end region 30. The transverse reinforcement channel 80 is concave with respect to the transverse axis T; however, the transverse reinforcement channel 80 may be convex with respect to the transverse axis T. As shown, the transverse reinforcement channel 80 can connect to the perimeter channel 75. The intersections of the transverse reinforcement channel 80 and the perimeter channel 75 can be disposed in the central region 32 or may be disposed in the back end region 30. It is believed that the transverse reinforcement channel 80 contributes to the overall structural integrity of the sanitary napkin 20. Particularly in the region located, adjacent the back end region 30, there can be a greater concentration of stress and strain due to movement of the wearer during use.

Herein, "channel" (or often referred to as "embossed channel") refers to a generally elongated depression formed in at least a portion of an absorbent article. The channel can be formed by compressing, embossing or otherwise modifying or directing the materials of the topsheet and the absorbent core at the channel portion in the manufacture process of absorbent articles.

Typically, the channel is formed by applying a compressive force to both the topsheet and at least a part of the absorbent core toward the backsheet. The material of the topsheet at the channel portion is pushed down into the absorbent core, and the materials of the topsheet and the absorbent core are compressed at and below the bottom of the channel portion. By this operation (which is often called "embossing process"), the channel portion of the absorbent article generally has relatively higher density than the other portion(s) or the surrounding portion(s) of the channel portion.

The channel tends to preferentially diffuse or lead body fluids flow along the direction in which the channel extends. Therefore, the channel is useful to control body fluids flow within the absorbent article thereby preventing body fluids leakage from the absorbent article. The channel also tends to work as a preferential bending axis of the absorbent article. Therefore, the absorbent article may bend at the channel portion such that it provides an improved fit of the absorbent article to the wearer's body. It should be noted that such an improved fit of the absorbent article can also contributes an improvement in preventing body fluids leakage from the absorbent article.

The channel of the present invention can be either continuous or discontinuous. Herein, "discontinuous" means the channel can be separated by a non-channel portion. Herein, "non-channel portion" refers to a portion of absorbent articles where no channel is formed between two component channel portions which are disposed in series. One discontinuous channel includes two or more component channel portions which are separated by a non-channel portion. The distance between the two component channel portions (i.e., the length of the no channel portion) may be changed depending on the product design. The length of the no channel portion can be, for example, from about 0 mm to about 20 mm, from about 2 mm to about 10 mm, or from about 3 mm to about 6 mm.

As shown, channels can be formed by applying two or more levels of compressive forces to the topsheet and the absorbent core toward the backsheet thereby forming a "two (or more) stage channel structure".

Referring now to FIGS. 1 and 2, all the channels described herein may be formed by applying two levels of compressive forces to the topsheet 38 and the absorbent core 42 toward the backsheet 40. The application of the two levels of compressive forces (i.e., higher compression and lower compression) produces two stage depth portions (i.e., "two stage channel structure") in the resulting the channels, i.e., first portion 81 and second portion 82. However, it is not necessary that all the channels be formed the same way or by the same process.

Figure 3:
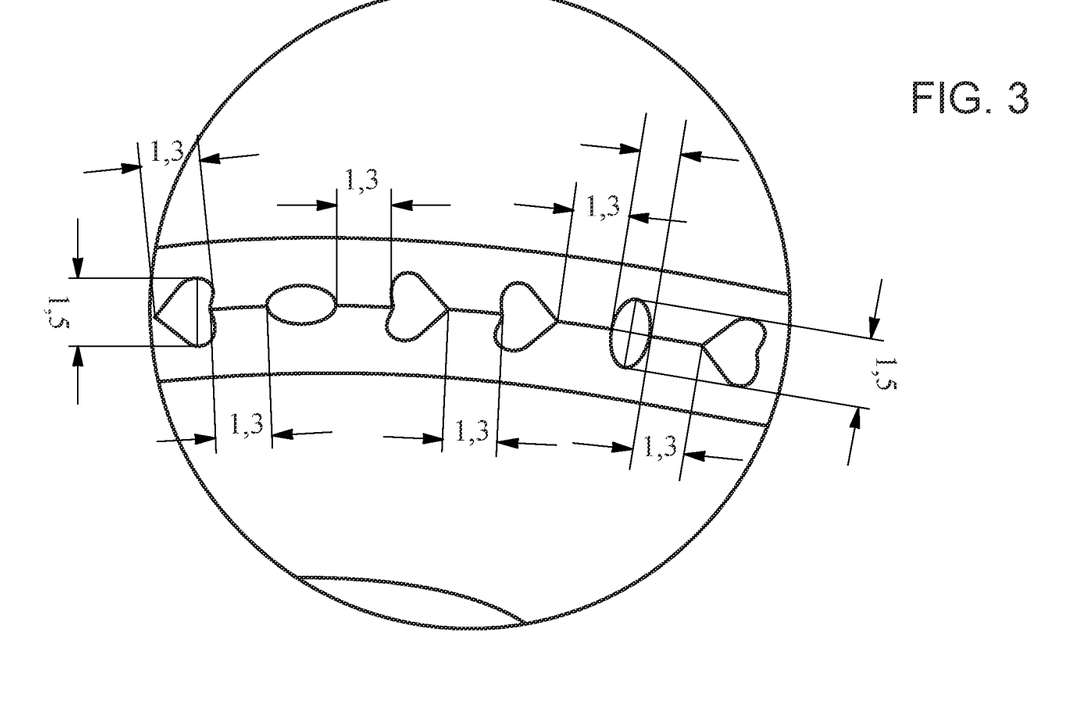
FIG. 3 is a close up view of a channel disposed on the absorbent article shown in FIG. 1.

Referring now to FIGS. 2 and 3, as shown, the perimeter channel 75 has two side walls (or channel walls) 83 and 84. The first portions 81 are formed by a higher compression, while the second portion 82 is formed by a lower compression. The absorbent core 42 is more compressed at the portions 81 of higher compression than the portion 82 of lower compression. The portions 81 of higher compression form the lowest portions of the channel 75, while the portion 82 of lower compression forms the higher portion in the channel 75. The first portions 81 of higher compression have a higher density than the portion 82 of lower compression as a result of compression force differences. Such a two stage channel structure may provide a better comfort to the wearer's body in use compared with the channel structure which has no stage difference (formed by no compression force differences applied). In addition, since the compression force is more concentrated at the portions 81 of higher compression, the two stage channel structure can also increase the bonding strength between the topsheet 38 and the absorbent core 42 at the portions 81.

Figure 4:
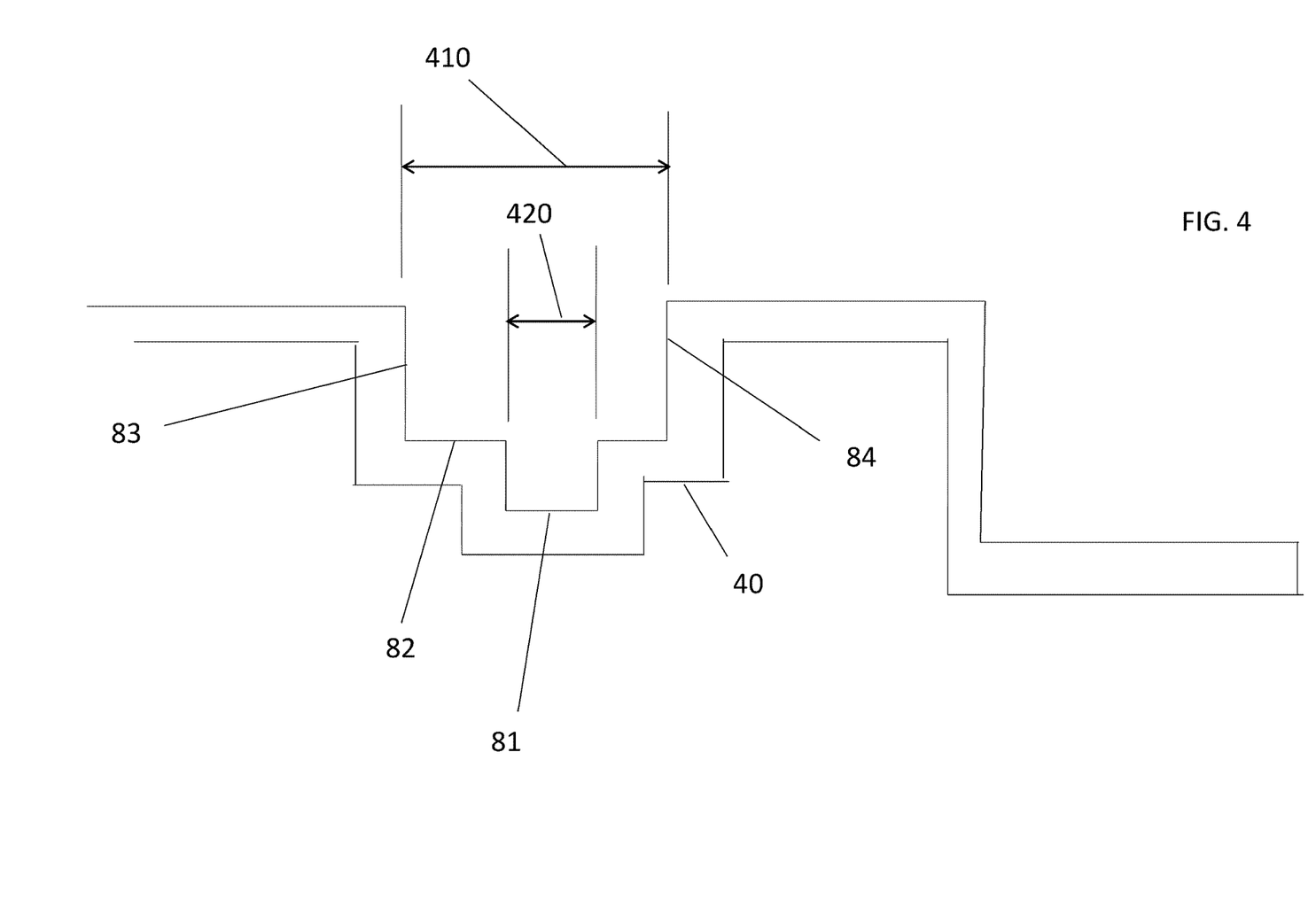
FIG. 4 is a close up view of the schematic cross section of FIG. 2.

Referring now to FIGS. 2-4, the first portions 81 formed by a higher compression are disposed offset from the channel walls 83 and 84. The shape of the first portions 81 formed by a higher compression can be any suitable shape. However, the shape of the first portions 81 can vary depending on the channel design in the sanitary napkin 20. The length, width 420 and depth of the first portions 81 can also vary depending on the channel design in the sanitary napkin 20. Similarly, the shape, the length, width 410 and depth of the second portion 82 can also vary depending on the channel design in the sanitary napkin 20. The first portions 81 are discrete and each adjacent first portion 81 is spaced apart from one another. Any suitable spacing between adjacent first portions can be utilized. As an example, the first portions 81 may be spaced apart by about 1.3 mm. Additionally, the width 420 of the first portions 81 can be any suitable width. It is worth noting that the width 420 of the first portions 81 is measured parallel to a perpendicular line to the side walls 83 and 84. The width 420 of the first portions 81 can be about 1.5 mm.

The width 410 of the second portion 82 can be any suitable distance. In one specific example, the width 410 of the second portion 82 may be about 2.8 mm. In another specific example, the width 410 of the second portion 82 may be about 3.0 mm. The width 410 of the second portion 82 can vary along the length of the channels described herein.

As stated previously, the channels of the present disclosure can provide increased integrity in the sanitary napkins constructed in accordance with the present disclosure. Additionally, the channels of the present disclosure can provide sanitary napkins constructed in accordance with the present disclosure with improved conformance for the wearer which can increase the comfort of the article during use.

As shown in Table 1, evaluation of the article integrity was investigated in accordance with the product integrity test disclosed herein. Comparative Example 1 is a commercially available pad sold under the trade name of "Private" produced by Sanita Products, an Egyptian company.

TABLE 1

| Product | PPF (N) |
| --- | --- |
| Always Ultra Maxi | 0.387 |
| Example 1 | 1.073 |
| Comparative Example 1 | 0.247 |

Example 1 was constructed as disclosed herein and included the channels described in FIGS. 1-3. Example 1 comprised a 22 gsm nonwoven, a fluff pulp core having a weight of 7.3 grams, and a polypropylene backsheet having a basis weight of 12 gsm.

As shown in Table 2, evaluation of dry bunch compression was performed in accordance with the bunch compression test disclosed herein. Comparative Example 2 is a commercially available pad sold under the trade name of "FAM" produced by Napco, a Saudi Arabian company.

TABLE 2

| Product | Value (N) |
| --- | --- |
| Always Ultra Maxi | 6.515 |
| Example 1 | 4.994 |
| Comparative Example 1 | 9.269 |
| Comparative Example 2 | 8.290 |

As shown in Table 3, evaluation of wet bunch compression was performed in accordance with the bunch compression test disclosed herein.

TABLE 3

| Product | Value (N) |
| --- | --- |
| Always Ultra Maxi | 5.062 |
| Example 1 | 4.345 |
| Comparative Example 1 | 10.444 |
| Comparative Example 2 | 8.420 |

The topsheet 38 is typically compliant, soft feeling, and non-irritating to the wearer's skin. Further, the topsheet 38 is generally at least partially liquid permeable or pervious, permitting body fluids (e.g., menses and/or urine) to readily penetrate through its thickness. A suitable liquid permeable material for the topsheet 38 may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet 38 includes a nonwoven web, the web may be manufactured by a wide number of known techniques. For example, the web may be spunbonded, carded, wet-laid, melt-blown, hydroentangled, combinations of the above, or the like.

A particularly suitable material for the topsheet 38 includes an apertured formed film. Apertured formed films are preferred for the topsheet 38 because they are pervious to body fluids and, if properly apertured, have a reduced tendency to allow liquids to pass back through and rewet the wearer's skin. Thus, the body surface of the formed film (i.e., the body surface 20A of the sanitary napkin 20) remains dry, thereby reducing body soiling and creating a more comfortable feel for the wearer. One material for use as the topsheet 38 is a macroscopically expanded, three-dimensional formed polyethylene film. One preferred material for the topsheet 38 is available from Tredegar Film Products, Indiana. USA, under Code No. X-15507.

The backsheet 40 is typically at least partially impervious to body fluids and is often manufactured from a thin plastic film, although other flexible materials may also be used. Herein, "flexible" refers to materials which are compliant and will readily conform to the general shape and contours of the human body. The backsheet 40 generally prevents the body fluids absorbed and contained in the absorbent core 42 from wetting articles which contact the absorbent article such as bed sheets, pants, pajamas and undergarments. The backsheet 40 may thus include a woven or nonwoven material, polymeric films such as thermoplastic films of polyethylene or polypropylene, or composite materials such as a film-coated nonwoven material. The backsheet 40 can include a single layer material, or two or more layers of materials. The backsheet 40 preferably has a thickness of from about 0.012 mm (0.5 mil) to about 0.081 mm (3.4 mils). In one embodiment, the backsheet 40 is a single layer polyethylene film. Such a preferred polyethylene film is available from Daedong Co. Ltd., KyungBuk-Do, Korea, under Code No. DNF-0417C-DG.

The backsheet 40 may have a microporous structure which can permit vapors to escape from the absorbent core 42 (often called "breathable backsheet") while still preventing body fluids from passing through the backsheet 40. One suitable microporous polyethylene film is available from Mitsubishi Chemical Corporation. Tokyo, Japan, under Code No. Espoir-N-PSF-B. The backsheet 40 can be embossed to provide a clothlike or any other desired appearance.

The absorbent core 42 is capable of receiving, absorbing or retaining body fluids discharged. The absorbent core 42 is generally compressible, conformable, and non-irritating to the wearer's skin. The absorbent core 42 can be formed by a single layer material or a plurality of layered materials. In one embodiment, the absorbent core 42 includes an acquisition layer or a secondary topsheet which quickly transports discharged body fluids received by the topsheet 38 to other parts of the acquisition layer and the absorbent core 50. The acquisition layer can temporarily hold such fluids until they can be absorbed by the other parts of the absorbent core 50. The distribution function of the acquisition layer is of particular importance in order to more fully utilize the capacity of the absorbent core 50. Thus, while the acquisition layer may comprise a wide variety of absorbent materials, it preferably comprises a fibrous material that can rapidly transport fluid and not collapse upon being wetted so that the acquisition layer can effectively acquire and distribute second and successive fluids.

The absorbent core may include any of a wide variety of liquid-absorbent materials commonly used in absorbent articles, such as comminuted wood pulp, which is generally referred to as airfelt. One suitable absorbent core material is an airfelt material which is available from Weyerhaeuser Company. Washington, USA, under Code No. FR516.

Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; absorbent gelling materials; or any equivalent material or combinations of materials, or mixtures of these.

The absorbent core 42 may be manufactured in a wide variety of sizes and shapes. The periphery of the absorbent core 42 thus can take any shape in its top plane view. The core periphery may be any suitable shape, include an oval, a rectangle, an hourglass, and a combination of the oval and rectangle.

The sanitary napkin 20 can be of any caliper, including relatively thick, relatively thin, or even very thin. The embodiment of the sanitary napkin 20 shown in FIG. 1 is intended to be an example of a relatively thick sanitary napkin having a caliper of about 4 mm in the end regions 28 and 30 and a caliper of about 6 mm in the central region 32. It should be understood, however, when viewing these figures the number of layers of material shown may cause the sanitary napkin 20 to appear much thicker than it actually is, particularly in cross-section.

The topsheet 38, the backsheet 40, and the absorbent core 42 may be assembled in a variety of configurations, sizes and shapes known in the art. Examples of suitable configurations are described in U.S. Pat. Nos. 4,950,264; 5,009,653 issued to Osborn; U.S. Pat. No. 4,425,130 issued to DesMarais; U.S. Pat. Nos. 4,589,876 and 4,687,478 issued to Van Tilburg, and U.S. Pat. No. 5,234,422 issued to Sneller, et al.

The topsheet 38 and the backsheet 40 typically have length and width dimensions generally larger than those of the absorbent core 42. The topsheet 38 and backsheet 40 extend beyond the edges of the absorbent core 42 and are joined together to form a pair of central side flaps 52. These topsheet 38 and backsheet 40 can be joined any means (e.g., an adhesive) known in the art.

Sanitary napkin 20 may be attached to the wearer's panties or undergarment through adhesive fasteners as known in the art. The fasteners comprise a plurality of patches of adhesive which are adhered to the garment surface 20B of the backsheet 40 of the sanitary napkin 20. Those fasteners include one or two (or more if desired) adhesive patches (i.e., panty fastening adhesive) that are disposed on the main body portion 25 of the sanitary napkin 20 such that the sanitary napkin 20 can adhere to the crotch area of the wearer's undergarment to keep the sanitary napkin 20 in place. Those fasteners also include a pair of additional adhesive patches (i.e., flap adhesives) that are disposed on the garment surface 20B of the central side flaps 52 of the sanitary napkin 20 to adhere to the undersides of the wearer's undergarment during use and to keep the napkin 20 in place to improve fit. Examples of suitable adhesive fastener structures including release strips are described in, for example, U.S. Pat. No. 6,074,376 issued to Mills on Jun. 13, 2000.

Test Methods
Product Integrity Via Pad Peel Force

This peel force test method is used to measure the force required to detach the topsheet and absorbent core (as one component) from the backsheet (garment-facing layer) of an absorbent article. Peel force is measured on a constant rate of extension tensile tester interfaced to a computer (a suitable instrument is the MTS Alliance using Testworks 4.0 software, as available from MTS Systems Corp., Eden Prairie, MN, or equivalent) using a load cell for which the forces measured are within 1%-99% of the limit of the cell. All testing is performed in a room controlled at 23° C.±3° C. and 50%±2% relative humidity and test samples are conditioned in this environment for at least 2 hours prior to testing.

A strip of 50.8 mm (2 inch) wide extra strong duct tape (Isover Vario Xtra Tape, available from amazon.com, or equivalent) is adhered to the body facing ("top") side and the garment facing ("bottom") side of the test sample as reinforcement to prevent undesired stretching of the chassis materials during the peel test (e.g. less than 2 mm of extension at the maximum peel force of the experiment). Fresh tape strips are used for each sample tested. A padded weight assembly is used to ensure adequate and even attachment of the reinforcement tape strips to the top and bottom sides of the test sample. The weight assembly must impart a pressure of 26-27 $g/cm^2$ with a base that has a width of 50.8 mm and a length about the same longitudinal length as that of the test sample. The weight assembly is constructed as follows. Lay a single layer of polyethylene film (0.02-0.04 mm thick; any convenient source) flat on a bench surface. A piece of flexible insulation foam (Buna-N/PVC, 1 inch thick, density of 4.5 pounds/cubic foot; available from McMaster-Carr, Princeton, NJ, or equivalent) that is cut to the predetermined base size is laid centered on top of the film. A metal weight (same length and width as the predetermined base size) with a handle is then attached to the insulation foam using double sided tape. Next the polyethylene film is wrapped around the insulation foam and secured to the sides of the metal weight using transparent tape.

To prepare the test sample, first remove it from any wrapper present. If the sample is folded, gently unfold it, smooth out any wrinkles and determine and mark which end of the sample is intended to be the rear end. If wings are present, unfold the wings. Place the test sample on a horizontally flat rigid surface with the top of the sample facing down. Remove the Panty Fastening Adhesive (PFA) protective cover, if present, and discard. Cut a strip of duct tape that is at least as long as the longitudinal length of the test sample. Center the tape strip about the longitudinal axis of the test sample and adhere the tape to the bottom side of the test sample without creating any wrinkles in the tape strip or sample. Place the prepared weight assembly centered over the tape strip and leave in place for 30 seconds. Now remove the weight assembly and set aside. Turn the test sample over so that the top side is now facing up. Cut a second strip of duct tape that has a length similar to the first tape strip. Align this tape strip with the strip already adhered to the bottom side of the test sample, then adhere it to the top side of the test sample without creating any wrinkles in the tape strip or sample. Place the prepared weight assembly centered over the tape strip. After 30 seconds, remove the weight assembly and set aside. Near each longitudinal end of the test sample, End Lines are drawn across the tape that are perpendicular to the longitudinal axis of the sample. The End Lines are located as close to the longitudinal ends of the test sample as possible while ensuring that the sample area inbound of these lines (within the tape strips) does not include any portion of an edge crimp or edge seal of the sample. Using scissors, cut along the End Lines at each end of the test sample and discard each portion that is cut away. Now cut the test sample into a 50.8 mm wide strip (centered about the longitudinal axis of the sample) where the lateral cuts correspond to the lateral edges of the tape strips and discard the portions that are cut away. Measure the longitudinal length of the prepared test sample using a calibrated ruler (NIST certified, or equivalent) and record as Sample$_L$ to the nearest mm. A total of five replicate test samples are prepared in like fashion for each product to be tested.

For this peel test, an identical set of grips are used to hold the test sample, with one attached to the lower fixture and the other attached to the upper fixture of the tensile tester. Ideally, the grips are manual and lightweight to maximize the capacity of the load cell, and they must be wider than the prepared test sample. The grips are constructed in such a way that a single line of gripping force along a line perpendicular to the pull axis of the tensile tester is enabled. The upper and lower grips are mounted in such a way that they are horizontally and vertically aligned.

Program the tensile tester for a constant rate of extension uniaxial elongation with a set path length as follows. The gauge length is set to 20 mm (bottom edge of upper grip to top edge of lower grip) and the crosshead is zeroed. The path length is governed by the length of the prepared test sample, Sample$_L$, and is set to a distance that is about 80 mm less than twice Sample$_L$ (e.g. if Sample$_L$ is 200 mm, the path length is set to 320 mm). This path length takes into account the portion of the sample that will be manually peeled and contained within the grips and allows for a portion at the end of the sample to prevent it from becoming fully detached during the peel. Just prior to inserting the test sample into the grips of the tensile tester, manually initiate a longitudinal peel between the strips of tape at the rear end of the test sample that is about 20 mm long. The top side of the initiated peel includes the tape, topsheet and absorbent core, and the bottom side of the initiated peel includes the backsheet and the other strip of tape. Now insert about 10 mm of the bottom side of the peeled portion of the test sample into the lower grip of the tensile tester. Ensure that the prepared test sample is centered within the grip and the longitudinal edge of the tape is parallel to the edge of the grip. In like fashion, insert about 10 mm of the top side of the peeled portion of the test sample into the upper grip of the tensile tester. With the prepared test sample mounted in this manner, the longitudinal length of the sample will be hanging somewhat perpendicular to the pull-axis of the tensile tester, and the weight of the hanging sample will be applying a force to the load cell. The load cell should now be zeroed. Raise the crosshead at a rate of 500 mm/min for the entire path length, collecting force (N) and extension (mm) data at 50 Hz throughout the test. Return the crosshead to its original location. Construct a graph of force (N) versus extension (mm).

Calculate the average force along the entire path length and record to the nearest 0.01 N. In like fashion, repeat the test for all five replicate test samples. Calculate the arithmetic mean for average force and report as Pad Peel Force (PPF) to the nearest 0.01 N.

Bunch Compression

Bunched Compression of a sample is measured on a constant rate of extension tensile tester (a suitable instrument is the MTS Alliance using Testworks 4.0 software, as available from MTS Systems Corp., Eden Prairie, MN, or equivalent) using a load cell for which the forces measured are within 10% to 90% of the limit of the cell. All testing is performed in a room controlled at 23° C.±3° C. and 50%±2% relative humidity. The test can be performed wet or dry.

Referring to FIGS. 5-7B, the bottom stationary fixture 3000 consists of two matching sample clamps 3001 each 100 mm wide each mounted on its own movable platform 3002a, 3002b. The clamp has a "knife edge" 3009 that is 110 mm long, which clamps against a 1 mm thick hard rubber face 3008. When closed, the clamps are flush with the interior side of its respective platform. The clamps are aligned such that they hold an un-bunched specimen horizontal and orthogonal to the pull axis of the tensile tester. The platforms are mounted on a rail 3003 which allows them to be moved horizontally left to right and locked into position. The rail has an adapter 3004 compatible with the mount of the tensile tester capable of securing the platform horizontally and orthogonal to the pull axis of the tensile tester. The upper fixture 2000 is a cylindrical plunger 2001 having an overall length of 70 mm with a diameter of 25.0 mm. The contact surface 2002 is flat with no curvature. The plunger 2001 has an adapter 2003 compatible with the mount on the load cell capable of securing the plunger orthogonal to the pull axis of the tensile tester.

Samples are conditioned at 23° C.±3° C. and 50%±2% relative humidity for at least 2 hours before testing. When testing a whole article, remove the release paper from any panty fastening adhesive on the garment facing side of the article. Lightly apply talc powder to the adhesive to mitigate any tackiness. If there are cuffs, excise them with scissors, taking care not to disturb the top sheet of the product. Place the article, body facing surface up, on a bench. On the article identify the intersection of the longitudinal midline and the lateral midline. Using a rectangular cutting die, cut a specimen 100 mm in the longitudinal direction by 80 mm in the lateral direction, centered at the intersection of the midlines. When testing just the absorbent body of an article, place the absorbent body on a bench and orient as it will be integrated into an article, i.e., identify the body facing surface and the lateral and longitudinal axis. Using a rectangular cutting die, cut a specimen 100 mm in the longitudinal direction by 80 mm in the lateral direction, centered at the intersection of the midlines.

The specimen can be analyzed both wet and dry. The dry specimen requires no further preparation. The wet specimens are dosed with 7.00 mL±0.01 mL 10% w/v saline solution (100.0 g of NaCl diluted to 1 L deionized water). The dose is added using a calibrated Eppendorf-type pipettor, spreading the fluid over the complete body facing surface of the specimen within a period of approximately 3 sec. The wet specimen is tested 15.0 min±0.1 min after the dose is applied.

Program the tensile tester to zero the load cell, then lower the upper fixture at 2.00 mm/sec until the contact surface of the plunger touches the specimen and 0.02 N is read at the load cell. Zero the crosshead. Program the system to lower the crosshead 15.00 mm at 2.00 mm/sec then immediately raise the crosshead 15.00 mm at 2.00 mm/sec. This cycle is repeated for a total of five cycles, with no delay between cycles. Data is collected at 100 Hz during all compression/decompression cycles.

Figure 5:
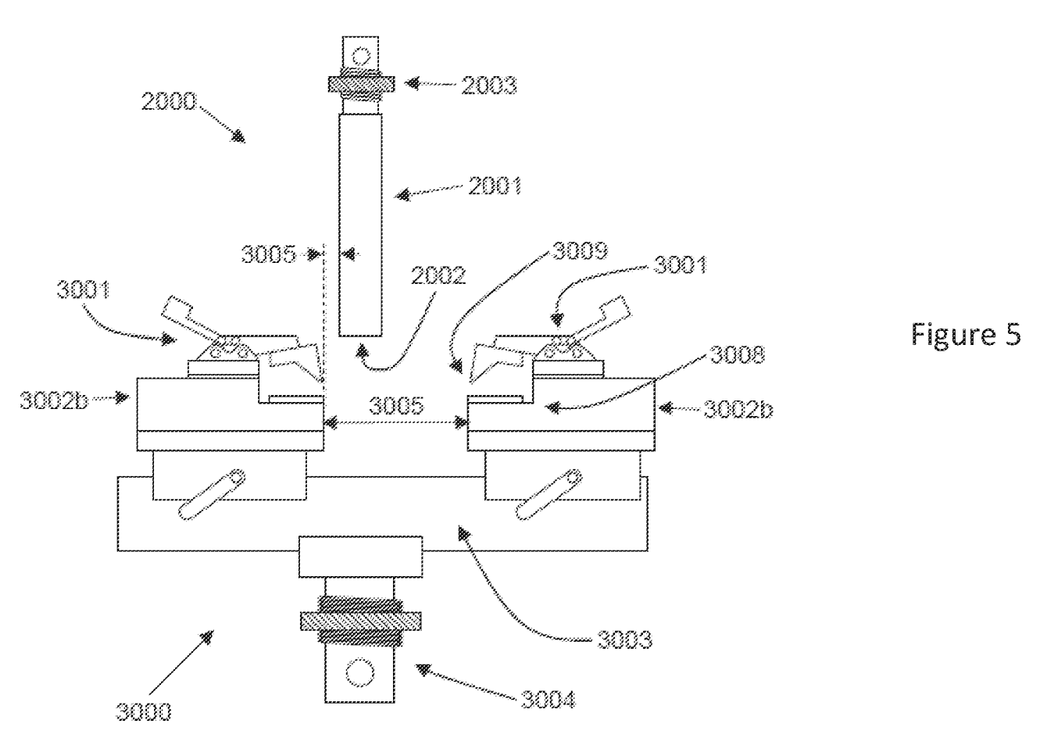
FIG. 5 is a schematic depiction showing an apparatus for the Bunch Compression test method as described herein.
Figure 6A:
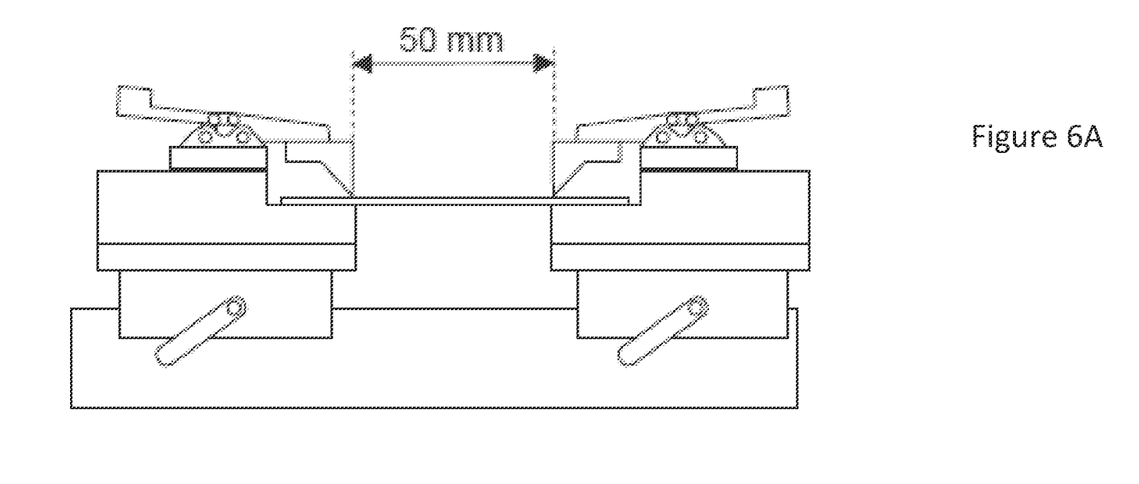
FIGS. 6A-B relate to the test method of FIG. 5.
Figure 6B:
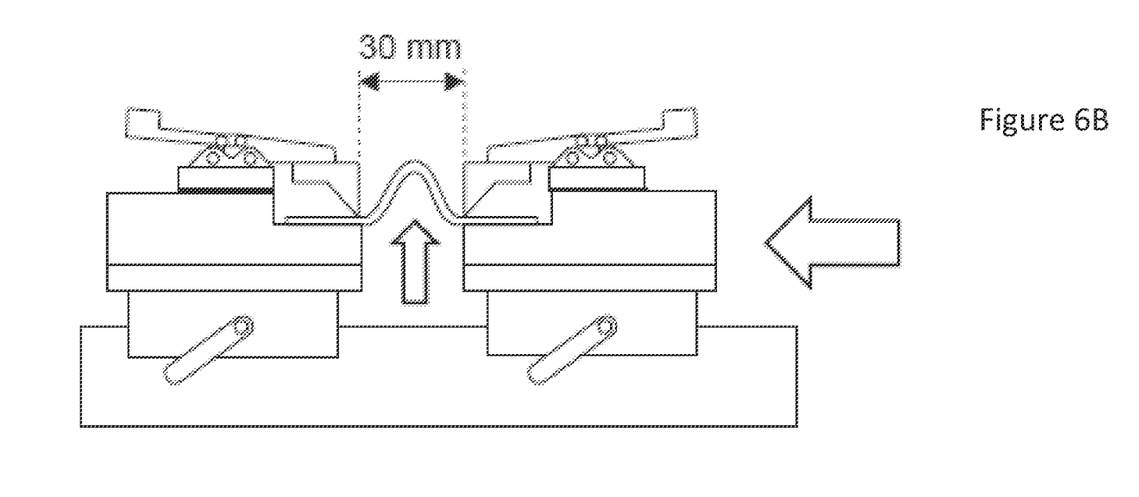

Position the left platform 3002a 2.5 mm from the side of the upper plunger (distance 3005). Lock the left platform into place. This platform 3002a will remain stationary throughout the experiment. Align the right platform 3002b 50.0 mm from the stationary clamp (distance 3006). Raise the upper probe 2001 such that it will not interfere with loading the specimen. Open both clamps. Place the specimen with its longitudinal edges (i.e., the 100 mm long edges) within the clamps. With the specimen laterally centered, securely fasten both edges. Move the right platform 3002b toward the stationary platform 3002a a distance 20.0 mm. Allow the specimen to bow upward as the movable platform is positioned. Manually lower the probe 2001 until the bottom surface is approximately 1 cm above the top of the bowed specimen.

Figure 7A:
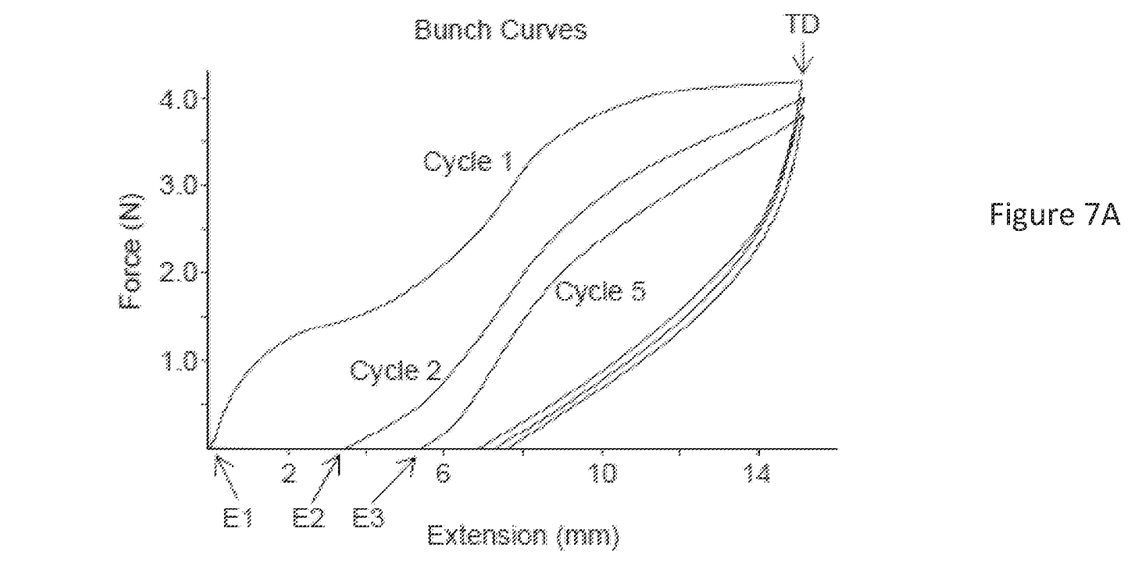
FIGS. 7A-B relate to the test method of FIG. 5.
Figure 7B:
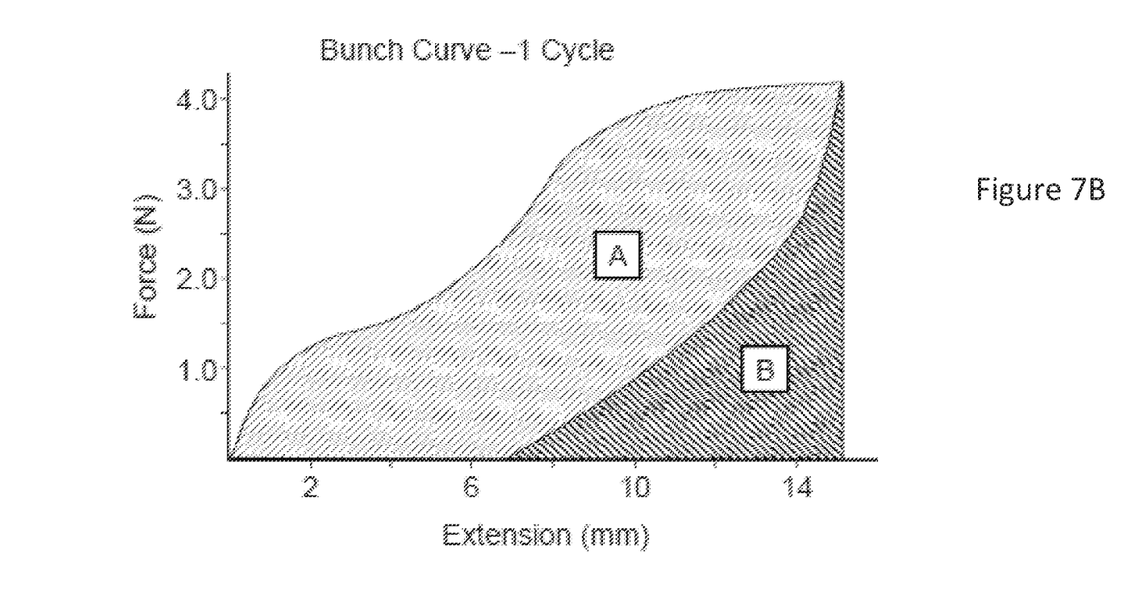

Start the test and collect displacement (mm) verses force (N) data for all five cycles. Construct a graph of Force (N) versus displacement (mm) separately for all cycles. A representative curve is shown in FIG. 7A. From the curve record the Maximum Compression Force for each Cycle to the nearest 0.01 N. Calculate the % Recovery between the First and Second cycle as (TD−E2)/(TD−E1)*100 where TD is the total displacement and E2 is the extension on the second compression curve that exceeds 0.02 N. Record to the nearest 0.01%. In like fashion calculate the % Recovery between the First Cycle and other cycles as (TD−$E_i$)/(TD−E1)*100 and report to the nearest 0.01%. Referring to FIG. 7B, calculate the Energy of Compression for Cycle 1 as the area under the compression curve (i.e., area A+B) and record to the nearest 0.1 mJ. Calculate the Energy Loss from Cycle 1 as the area between the compression and decompression curves (i.e., Area A) and report to the nearest 0.1 mJ. Calculate the Energy of Recovery for Cycle 1 as the area under the decompression curve (i.e. Area B) and report to the nearest 0.1 mJ. In like fashion calculate the Energy of Compression (mJ), Energy Loss (mJ) and Energy of Recovery (mJ) for each of the other cycles and record to the nearest 0.1 mJ For each sample, analyze a total of five (5) replicates and report the arithmetic mean for each parameter. All results are reported specifically as dry or wet including test fluid (0.9% or 10%).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
   a front end region, a back end region, and a central region disposed therebetween;
   a topsheet;
   a backsheet;
   an absorbent core disposed between the topsheet and the backsheet;
   embossed central channels disposed in the central region;
   a perimeter channel, wherein the outwardly convex transverse channels are disposed inboard of the perimeter channel;
   a pair of rear channels disposed in the back end region and being disposed transversely inboard of the perimeter channel and longitudinally outboard of the outwardly convex longitudinal channels, wherein:
   the pair of rear channels are disposed on opposite sides of a longitudinal axis,
   the pair of rear channels are candy cane-shaped,
   the pair of rear channels are inwardly convex, and
   a transverse reinforcement channel joined to opposite sides of the perimeter channel, wherein the transverse reinforcement channel is disposed between the outwardly convex transverse channels and the rear channels.

2. The disposable absorbent article of claim 1, wherein the absorbent core comprises absorbent fluff pulp and is absent of super absorbent polymer.

3. The disposable absorbent article of claim 1, wherein the absorbent article has a dry bunch compression value of less than 6.0N.

4. The disposable absorbent article of claim 1, wherein the perimeter channel further comprises a pair of inwardly convex longitudinal channels disposed inboard of the outwardly convex longitudinal channels.

5. The disposable absorbent article of claim 1, further comprising a pair of front channels disposed in the front end region and being disposed transversely inboard of the perimeter channel.

6. The disposable absorbent article of claim 5, wherein the pair of front channels are disposed on opposite sides of the longitudinal axis.

7. The disposable absorbent article of claim 5, wherein the pair of front channels are disposed longitudinally outboard of the outwardly convex longitudinal channels.

8. The disposable absorbent article of claim 1, wherein each of the embossed central channels comprises opposing sidewalls, a first portion forming a first bottom surface of the central channel, and a second portion forming a second bottom surface of the central channel, wherein the second bottom surface is subjacent the first bottom surface.

9. The disposable absorbent article of claim 8, wherein the second portion is discrete and is surrounded by the first portion.

10. The disposable absorbent article of claim 9, wherein the second portion does not contact either of the sidewalls of the embossed central channels.

11. The disposable absorbent article of claim 1, wherein the perimeter channel, the pair of front channels, and the pair of rear channels each comprise opposing side walls, a first portion forming a first bottom surface of each of the perimeter channel, the pair of front channels and the pair of rear channels, and a second portion forming a second bottom surface of each of the perimeter channel, the pair of front channels and the pair of rear channels, wherein the second bottom surface is subjacent the first bottom surface.

12. The disposable absorbent article of claim 1, wherein the perimeter channel is continuous.

13. The disposable absorbent article of claim 1, wherein the perimeter channel extends from the front end region to the back end region.

14. The disposable absorbent article of claim 1, wherein the embossed central channels comprise outwardly convex transverse channels and outwardly convex longitudinal channels, wherein the outwardly convex transverse channels and the outwardly convex longitudinal channels are joined together.

* * * * *